United States Patent [19]

Baltes et al.

[11] 4,355,187

[45] Oct. 19, 1982

[54] PROCESS FOR THE MANUFACTURE OF METHYL GLYOXAL

[75] Inventors: Herbert Baltes, Frankfurt am Main; Ernst I. Leupold, Neu-Anspach, both of Fed. Rep. of Germany

[73] Assignee: Hoechst Aktiengesellschaft, Frankfurt am Main, Fed. Rep. of Germany

[21] Appl. No.: 247,914

[22] Filed: Mar. 26, 1981

[30] Foreign Application Priority Data

Mar. 28, 1980 [DE] Fed. Rep. of Germany ....... 3012004

[51] Int. Cl.³ .................. C07C 45/29; C07C 45/32
[52] U.S. Cl. ................................. 568/471; 568/470; 568/473; 568/474
[58] Field of Search ............... 568/471, 474, 473, 470

[56] References Cited

U.S. PATENT DOCUMENTS

| | | | |
|---|---|---|---|
| 2,051,266 | 8/1936 | McAllister et al. | 568/471 |
| 2,339,282 | 1/1944 | McMamee | 568/471 |
| 2,339,346 | 1/1944 | McMamee et al. | 568/471 |
| 2,339,348 | 1/1944 | McMamee | 568/471 |
| 2,849,493 | 8/1958 | Shelton et al. | 568/471 |
| 4,242,282 | 12/1980 | Diem et al. | 568/471 |

FOREIGN PATENT DOCUMENTS

| | | | |
|---|---|---|---|
| 918746 | 8/1954 | Fed. Rep. of Germany | 568/471 |
| 1032732 | 6/1958 | Fed. Rep. of Germany | 568/471 |
| 1923048 | 7/1979 | Fed. Rep. of Germany | 568/471 |
| 576877 | 4/1946 | United Kingdom | 568/471 |

OTHER PUBLICATIONS

Houben-Weyl, "Methoden oder organishen Chemie", vol. V11/12, pp. 771 et seq., V11/2, p. 708, vol. V111/1, p. 235, (1943).

Sander et al., "Ind. Eng. Chem.", vol. 46, pp. 414–426, (1954).

Primary Examiner—Werren B. Lone
Attorney, Agent, or Firm—Curtis, Morris & Safford

[57] ABSTRACT

Methyl glyoxal is prepared by oxidation of propylene glycol-1,2 in the gaseous phase on a heterogeneous catalyst. The process is carried out with an excess of oxygen and the catalyst used contains molybdenum and at least one of the metals: vanadium, silver, copper, iron, tungsten, tin, zinc, alkali metals, alkaline earth metals.

3 Claims, No Drawings

PROCESS FOR THE MANUFACTURE OF METHYL GLYOXAL

The present invention relates to a process for the manufacture of methyl glyoxal by oxidation of propylene glycol-1,2 in the gaseous phase on a heterogeneous catalyst.

It is known from U.S. Pat. No. 2,051,266 that a glycol of formula I may be oxidized with molecular oxygen in substoichiometric quantity in the presence of a catalyst to yield the corresponding dicarbonyl compound of formula II:

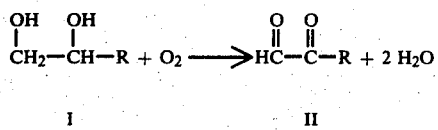

$$\underset{I}{\overset{OH\ \ \ OH}{\underset{|\ \ \ \ \ |}{CH_2-CH-R}}} + O_2 \longrightarrow \underset{II}{\overset{O\ \ \ O}{\underset{\|\ \ \ \ \|}{HC-C-R}}} + 2\ H_2O$$

By using a quantity of oxygen lower than the stoichiometric amount the dicarbonyl compound II undergoes no further oxidation in secondary reactions to yield, for example, the corresponding carboxylic acid, or, as a result of a cleavage of C-C bonds, formaldehyde or carbon oxides. Using a quantity of oxygen lower than the stoichiometric amount has the disadvantage that there are also formed products of lower oxidation number than the desired products, for example hydroxycarbonyl compounds. A further disadvantage is that an incomplete conversion of the starting product I and thus losses in yield as well as separation problems have to be taken into consideration. Unreacted glycol I reacts furthermore with the dicarbonyl compound II obtained to yield high boiling, stable acetals or other high molecular weight condensation products. This also causes losses in yield and considerable separation problems (cf. U.S. Pat. No. 2,339,346).

Suitable catalytically active metals according to said U.S. Pat. No. 2,051,266 are above all the subgroup elements of the fourth period (titanium to zinc), in particular copper.

Several modifications have been proposed to avoid the disadvantages involved in the process for the manufacture of methyl glyoxal from propylene glycol-1,2 according to U.S. Pat. No. 2,051,266:

In U.S. Pat. No. 2,339,346 there are added small amounts of halogens or organic halogen compounds, while using an excess of oxygen. However, this addition obviously gives rise to problems concerning the reactor material and complicates a working up. As catalysts suitable for this process there are mentioned in particular copper and silver. This oxidation of propylene glycol-1,2 yields only 68% of methyl glyoxal in addition to 7% of formaldehyde and formic acid.

In the process disclosed in German Pat. No. 857,359 there are used only from 10 to 50% of the theoretically required quantity of oxygen. This process results in a methyl glyoxal yield of only 50% and in an incomplete conversion of propylene glycol-1,2 involving the above-described disadvantages.

German Pat. No. 1,923,048 discloses a process for oxidizing propylene glycol-1,2 to yield methyl glyoxal, wherein there are used
(a) copper, silver and/or gold and
(b) an element of the fourth and/or fifth main group of the periodic table, as catalytically active metals. This process gives a yield of methyl glyoxal of about 70% at a conversion rate of 93%. A simple working up is, however, impaired due to this incomplete conversion and to the formation of 1-hydroxypropanone.

Czechoslovakian Pat. Nos. 140,414 and 119,683 propose processes resulting in a propylene glycol-1,2 conversion rate of at most 53% when working in the presence of silver catalysts at a temperature of from 530° to 600° C. In addition to this unsatisfactory conversion rate and the problems involved therewith, this process has the disadvantage that the relatively high reaction temperature imposes great requirements on the apparatuses used.

All of the above-described processes are unsatisfactory with respect to their yields and to a simple, economic operation.

The present invention was therefore concerned with the task of providing a process to obviate the problems previously encountered, namely—the formation of products having a lower oxidation number than the desired products,
secondary reactions of the methyl glyoxal obtained with unreacted propylene glycol-1,2,
contamination by auxiliary substances. This task is fulfilled according to the invention by using a special catalyst system in combination with an excess of oxygen.

The present invention therefore is in a process for the manufacture of methyl glyoxal by oxidation of propylene glycol-1,2 in the gaseous phase on a heterogeneous catalyst, which comprises using an excess of oxygen and a catalyst system containing molybdenum and at least one of the following elements: vanadium, silver, copper, iron, tungsten, tin, zinc, alkali metals and alkaline earth metals.

As compared to the known processes this process is distinguished by far higher yields and by a nearly quantitative conversion of propylene glycol-1,2. The expected formation of cyclic acetals (dioxolanes) from unreacted propylene glycol-1,2 and the methyl glyoxal formed are practically unobservable. Products having a lower oxidation number do not occur and no auxiliary substances are used. This simplifies working up of the product considerably.

In the process of the invention propylene glycol-1,2 is evaporated alone or as aqueous solution and is subsequently passed over the catalyst with oxygen or an oxygen-containing gas, in particular air.

It has proved advantageous to admix additionally to the reactants a carrier gas that is inert under the reaction conditions. Suitable carrier gases are, for example nitrogen or noble gases, but lower hydrocarbons such as methane, ethane or propane may likewise be used.

Air, when used as oxygen-containing gas, likewise acts as carrier gas.

The following amounts of additives are used in the process of the invention, per mol of propylene glycol-1,2: 0 to 15 mols, preferably 0 to 5 mols, of water, 1.2 to 10 mols, preferably 1.5 to 5 mols, of oxygen and 0 to 80 mols, preferably 10 to 80 mols, in particular 40 to 60 mols, of carrier gas.

Satisfactory results are even obtained, however, when using quantities beyond these limits.

The catalyst contains in addition to molybdenum at least one of the following elements: vanadium, silver, copper, iron, tungsten, tin, zinc, alkali metals, alkaline earth metals; vanadium, silver, copper, sodium, potassium, magnesium, barium being used preferably; vanadium, silver, sodium or potassium being used more preferably.

Catalysts containing molybdenum, vanadium and at least one of the following elements: silver, sodium, potassium, in particular silver, have proved particularly advantageous.

Said elements are introduced into the reaction zone either in metallic form or in the form of their compounds, for example as oxides, nitrates, acetates, acetylacetonates, oxalates, citrates or halides.

It has proved advantageous to pass an oxidizing gas, in particular oxygen or air, over the catalyst, at a temperature of from 100° to 800° C., in particular of from 300° to 600° C., prior to the reaction, in order to activate the catalyst.

The catalytically active elements are preferably applied to carrier materials. Suitable carriers are especially silicates, alumina, aluminium silicates, pumice or the different types of carbon, in particular silicates, alumina or aluminum silicates. Most advantageous are aluminum silicates and alumina, having a BET surface of less than 20 m$^2$/g, especially $\alpha$-alumina.

The total quantity of catalytically active elements may vary within wide limits. It is generally in the range of from 0.01 to 50 weight %, preferably of from 0.5 to 20 weight %, relative to the total quantity of supported catalyst. The weight ratio of molybdenum to the total quantity of the other catalytically active elements applied on the carrier is in general of from 1:0.01 to 1:10, preferably of from 1:0.1 to 1:2.

The catalytically active components are applied to the carrier preferably in the form of a solution, whereupon the solvent is evaporated and the catalyst dried. Suitable solvents are in general water, hydrochloric acid, nitric acid, aqueous alkali hydroxide solutions, or aqueous ammonia solution, preferably water or aqueous ammonia solution.

The active components may alternatively be used without a carrier.

The process according to the invention is generally carried out at a temperature of from 100° to 600° C., preferably of from 200° to 450° C.

The residence time is generally in the range of from 0.1 to 10 seconds, in particular of from 0.01 to 1 second. Satisfactory results are also obtained, however, beyond these limits.

The process according to the invention is carried out preferably under normal pressure, however, a reduced or elevated pressure (of from 0.01 to 100 bar) may be applied alternatively.

A suitable operation mode will be described hereinafter: Propylene glycol-1,2 or a mixture of propylene glycol and water is introduced into an evaporation zone by a metering device and the gas evolved is subsequently passed through an externally heated reaction tube charged with the catalyst. The above components are admixed to oxygen or to the oxygen-containing gas and to the carrier gas, if any, in the evaporation zone. It has proved advantageous to heat these gases to the reaction temperature prior to admixing them to the above components. After having left the reactor, the reaction products are cooled in order to separate the condensable portions therefrom. Methyl glyoxal may be isolated from the condensed product by usual methods, for example by rapid distillation according to German Pat. No. 1,914,038 or in the form of dimethyl acetal according to U.S. Pat. No. 2,866,823.

The condensate obtained when using a mixture of propylene glycol-1,2 and water is an aqueous solution which may be used directly in many fields, for example for the manufacture of acetals of methyl glyoxal (cf. U.S. Pat. No. 2,421,559).

Owing to their high reactivity, methyl glyoxal and the acetals of methyl glyoxal are suitable as intermediates for the manufacture of a great number of chemical compounds, for example highly effective insecticides of the allethrine type (cf. H. J. Sanders and A. W. Taff, Ind. Eng. Chem. 46, 414–426/1954/).

The following examples illustrate the invention:

EXAMPLE 1

12 ml/h of a 50% aqueous propylene glycol-1,2 solution are injected by means of a syringe into a vertically arranged glass reactor of 150 mm length and of 20 mm diameter via an evaporation zone. 56 Nl/h (Nl=liters measured under normal conditions i.e., 1 bar and 0° C.) of nitrogen and 7.4 Nl/h of oxygen, both preheated to 350° C., being simultaneously conveyed to the evaporation zone.

The reactor is also externally heated to 350° C. It is charged with 15 ml of an aluminum silicate catalyst containing 4.9 weight % of molybdenum and 5.1 weight % of vanadium and having a BET surface of about 1 m$^2$/g.

The catalyst is prepared by dissolving the calculated quantity of ammonium molybdate (NH$_4$)$_2$MoO$_4$ and ammonium vanadate (NH$_4$VO$_3$) in concentrated ammonia solution, by subsequently impregnating the catalyst carrier with the solution obtained and by evaporating the solvent on a steambath. The catalyst is then dried at 110° C. and subsequently heated for 3 hours to 400° C. in a reactor in a gas current consisting of 56 Nl/h of nitrogen and of 3 Nl/h of oxygen.

The temperature inside the reactor is measured by means of a thermoelement. The reaction products are condensed in a cooling trap at −70° C.

The actual catalyst test is carried out over a period of 2 hours after an initial period of 1 hour, during which constant operation conditions have set up. The condensate is analyzed by way of liquid chromatography.

After a 2 hours' test there are obtained 102 mmols of methyl glyoxal corresponding to a yield of 63%. The conversion rate of propylene glycol-1,2 is 98%. The yield of dioxolanes, relative to the propylene glycol-1,2 fed in, is smaller than 1%.

EXAMPLE 2

12 ml/h of a 50% aqueous propylene glycol-1,2 solution, 7.4 Nl/h of oxygen and 56 Nl/h of nitrogen are introduced into the apparatus as described in Example 1 in the manner described in Example 1. The reactor is charged with 15 ml of a catalyst containing 6 weight % of vanadium pentoxide, 3 weight % of molybdenum trioxide and 0.2 weight % of silver applied on an alpha-aluminum carrier (BET surface of about 1 m$^2$/g) and which is heated to 350° C.

After a 2 hours' test there are obtained 134 mmols of methyl glyoxal corresponding to a yield of 83%. The conversion rate of propylene glycol-1,2 is greater than 99%.

EXAMPLE 3

12 ml/h of a 50% aqueous propylene glycol-1,2 solution, 3.7 Nl/h of oxygen and 56 Ml/h of nitrogen are introduced into the apparatus as described in Example 1 in the manner described in Example 1. The reactor is charged with 15 ml of an aluminum silicate catalyst containing 3.8 weight % of molybdenum, 2.0 weight % of vanadium, 4 weight % of silver and 0.3 weight % of copper on a carrier as specified in Example 1 and which is heated to 330° C.

After a two hours' test there are obtained 123 mmols of methyl glyoxal corresponding to a yield of 76%. The conversion rate of propylene glycol-1,2 is 96%.

EXAMPLE 4

6 ml/h of propylene glycol-1,2 and 18.5 Nl/h of air are introduced into the apparatus specified in Example 1 in the manner described in Example 1. The reactor is charged with 15 ml of an aluminum silicate catalyst containing 4.0 weight % of molybdenum, 3.0 weight % of vanadium, 1.0 weight % of zinc, 1.0 weight % of tin and 1.0 weight % of tungsten on a carrier as specified in Example 1 and which is heated to 300° C.

After a two hours' test there are obtained 113 mmols of methyl glyoxal corresponding to a yield to 69%. The conversion rate of propylene glycol-1,2 is 94%.

EXAMPLE 5

12 ml/h of a 50% aqueous propylene glycol-1,2 solution, 3.7 Nl/h of oxygen and 56 Nl/h of nitrogen are introduced into the apparatus specified in Example 1 in the manner described in Example 1. The reactor is charged with 15 ml of an aluminum silicate catalyst containing 4.9 weight % of molybdenum, 5.1 weight % of vanadium, 0.45 weight % of potassium, 0.45 weight % of magnesium and 0.23 weight % of iron on a carrier as specified in Example 1 and which is heated to 350° C.

After a two hours' test there are obtained 118 mmols of methyl glyoxal corresponding to a yield of 73%. The conversion rate of propylene glycol-1,2 is 98.6%.

We claim:

1. A process for the manufacture of methyl glyoxal which comprises oxidizing propylene glycol-1,2 in the gaseous phase with an excess of oxygen and in the presence of a heterogeneous catalyst containing molybdenum in admixture with at least one element selected from the group consisting of vanadium, silver, copper, sodium, potassium, magnesium and barium.

2. The process of claim 1 wherein the catalyst contains molybdenum in admixture with at least one element selected from the group consisting of vanadium, silver, sodium and potassium.

3. The process of claim 1 wherein the catalyst contains molybdenum in admixture with vanadium and silver.

* * * * *